United States Patent [19]

Kesling

[11] 4,195,046
[45] Mar. 25, 1980

[54] METHOD FOR MOLDING AIR HOLES INTO A TOOTH POSITIONING AND RETAINING APPLIANCE

[76] Inventor: Peter C. Kesling, Green Acres, La Porte, Ind. 46320

[21] Appl. No.: 902,874

[22] Filed: May 4, 1978

[51] Int. Cl.² .............. A61C 13/00; B29C 5/00; B29H 3/00
[52] U.S. Cl. .................. 264/16; 264/219; 264/222; 264/275; 264/313; 264/317; 264/334; 433/6
[58] Field of Search .................. 264/16–18, 264/313, 317, 275, 334; 32/14 B, 14 C

[56] References Cited

U.S. PATENT DOCUMENTS

| | | | |
|---|---|---|---|
| 2,030,524 | 2/1936 | Lambert | 425/DIG. 44 |
| 2,152,738 | 4/1939 | Jeffrey | 425/DIG. 44 |
| 2,524,737 | 10/1950 | Sawyer | 425/DIG. 44 |
| 2,775,036 | 12/1956 | Kesling | 32/14 C |
| 2,880,509 | 4/1959 | Strickler | 32/14 B |
| 3,060,935 | 10/1962 | Riddell | 32/14 B |
| 3,233,310 | 2/1966 | Corl | 264/317 |
| 3,457,916 | 7/1969 | Wolicki | 32/14 C |
| 3,478,742 | 11/1969 | Bohlmann | 32/14 C |
| 3,502,755 | 3/1970 | Murray | 264/317 |
| 3,724,075 | 4/1973 | Kesling | 32/14 C |
| 3,837,081 | 9/1974 | Kesling | 32/14 C |
| 4,027,845 | 6/1977 | Putzer | 425/DIG. 44 |

Primary Examiner—W. E. Hoag
Attorney, Agent, or Firm—Lloyd L. Zickert

[57] ABSTRACT

Method for making a tooth positioning and retaining appliance with air holes. The apparatus includes a mold with a cavity having models of the upper and lower teeth arranged so that when an appliance is molded thereby the appliance will have upper and lower archways for receiving upper and lower arches of a person, tooth sockets in the archways arranged in ideal relationship and preselected positions to urge the teeth received thereby into the preselected positions of the sockets. The mold additionally includes air hole or airway forming means extending across the models of the teeth in the mold and being insertable into the mold prior to the molding operation and thereafter removable from the mold with the molded appliance. The air hole forming means is easily separable from the appliance to ultimately define the air holes between the archways and between the labial and lingual sides of the appliance. The method of making the air holes concerns the handling of the mold and the air hole forming means.

6 Claims, 12 Drawing Figures

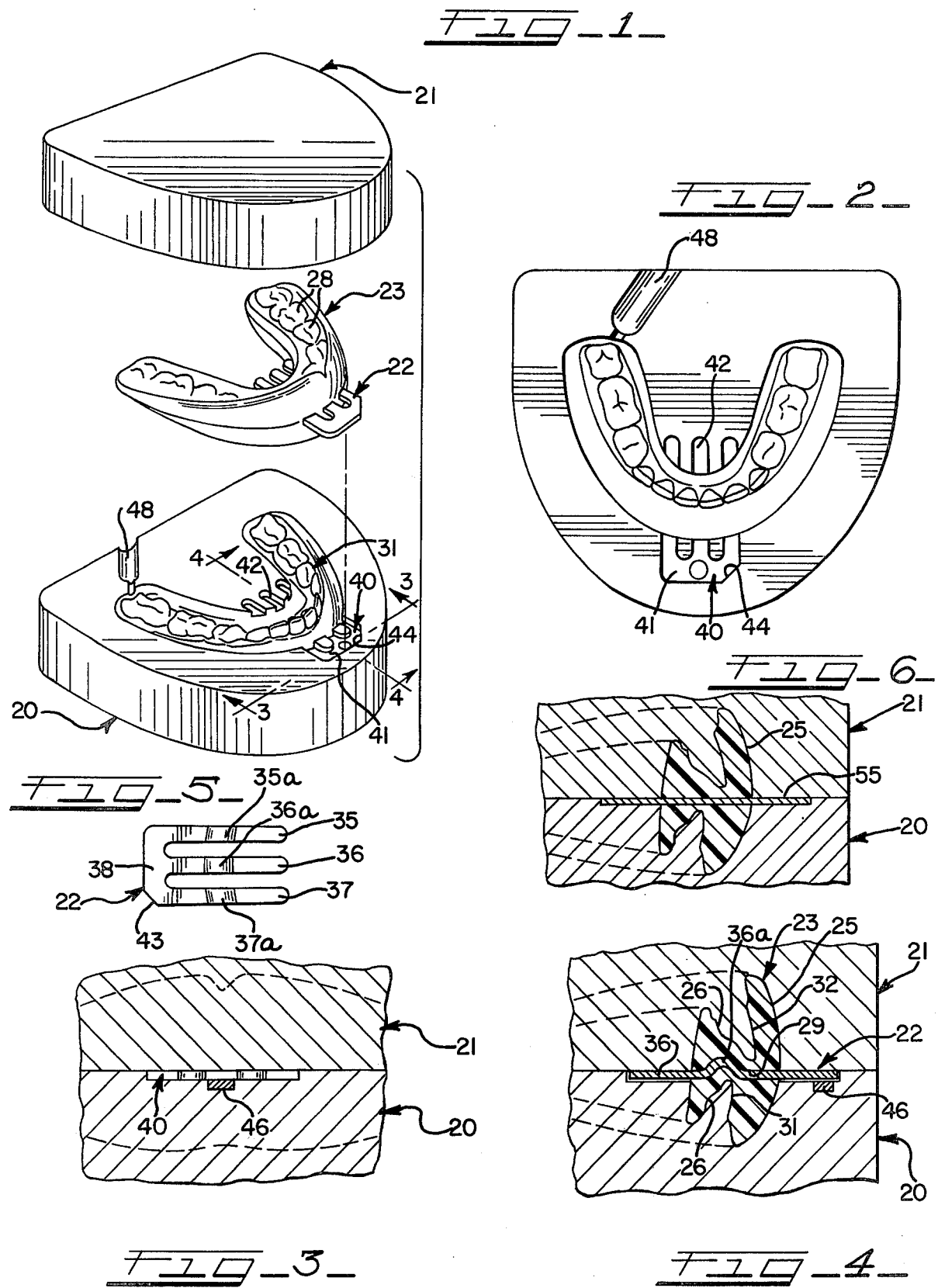

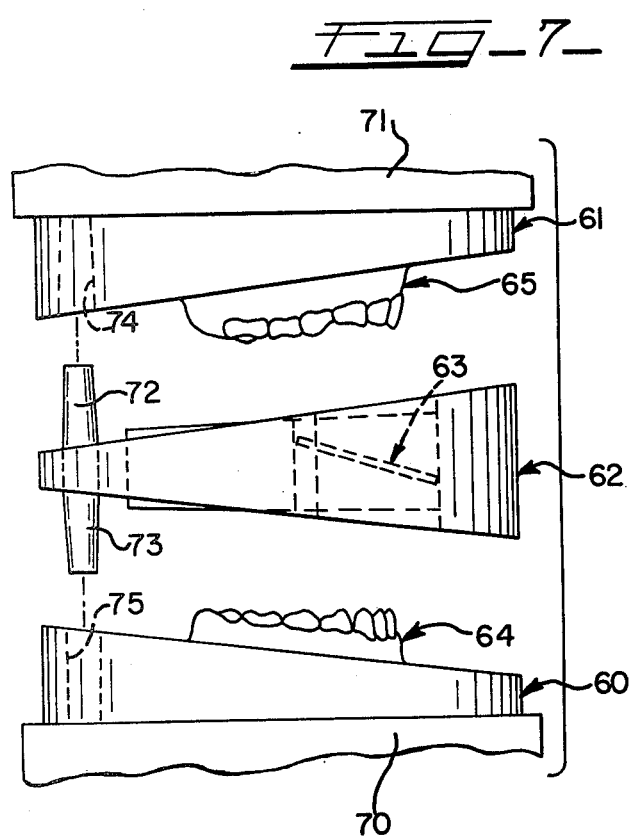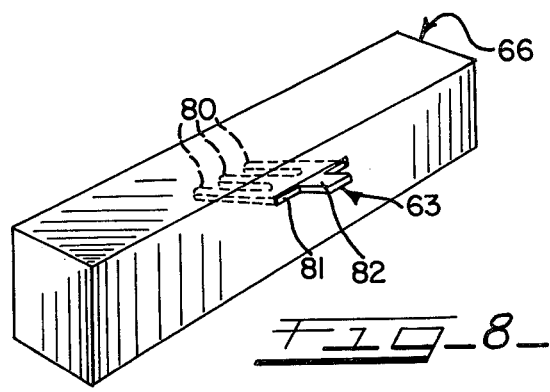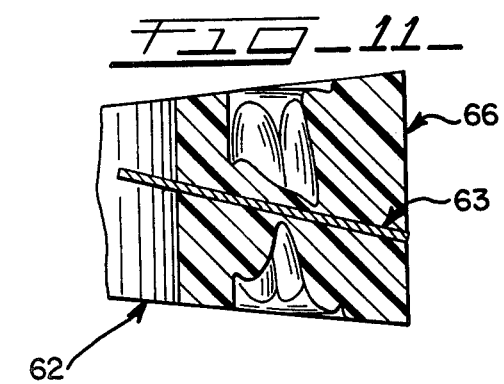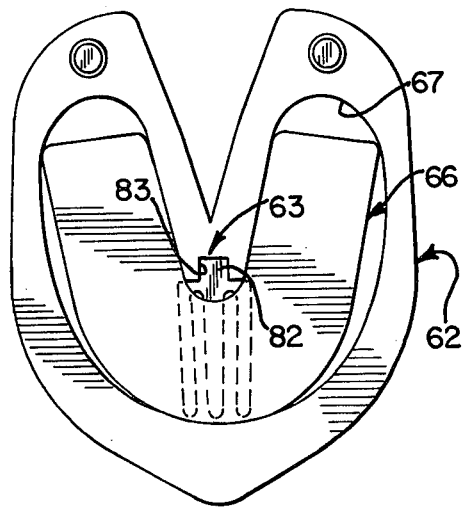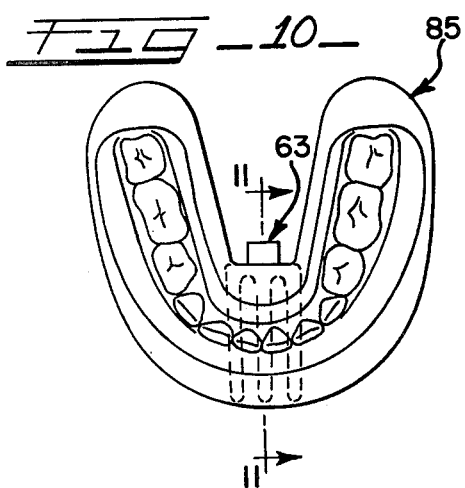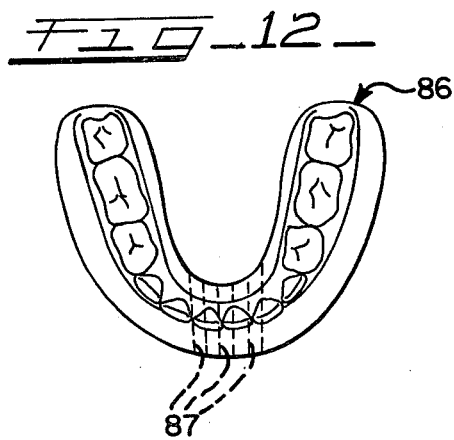

METHOD FOR MOLDING AIR HOLES INTO A TOOTH POSITIONING AND RETAINING APPLIANCE

This invention relates in general to a method and apparatus for making air holes or airways in a tooth positioning and retaining appliance and to an appliance having molded air holes in the freeway space between the upper and lower archways of the appliance.

Tooth positioning and retaining appliances, both custom made and preformed, are well known. Apparatus and method for making such appliances are also well known, such as that disclosed in U.S. Pat No. 2,775,036, which is designed to make custom appliances for a given patient. Preformed appliances are well known, such as illustrated in U.S. Pat. Nos. 3,724,075, 3,837,081, and other U.S. patents. Moreover, it is well known to provide air holes or airways in such appliances to assist the wearer to breathe through the mouth, but such air holes have been heretofore made by drilling same in the appliances after the appliances have been constructed. Drilling air holes in appliances has been unsatisfactory, whether the appliance material is clear or opaque, inasmuch as a hole drilled through a tooth socket which when mating with a tooth would be closed, thereby eliminating its function. Another problem heretofore encountered when drilling air holes in an appliance that would have a tooth socket fitted with a metal liner would be that the liner might be destroyed if in the path of the drill, thereby eliminating the purpose of the liner and requiring the appliance to be remade. While difficulty is encountered in drilling holes in an appliance made of clear material, it is even more difficult if the appliance is made of opaque material.

The present invention overcomes the difficulties heretofore known in connection with providing air holes or airways in tooth positioning and retaining appliances where the appliances may be custom made or preformed. The difficulties are overcome by molding the airways in the appliance during the fabrication procedure and which avoids any interference between airways and tooth sockets. The present invention accomplishes the objective by providing a mold with the usual models of teeth or arches in a cavity with air hole forming means insertable in the mold across the upper and lower arches of the teeth and being removable with the molded appliance when it is removed from the mold. Thereafter, the air hole forming means is easily separated from the molded appliance to define the air holes. By controlling the manner in which the air hole forming means coacts with the models of the teeth, the air holes are molded between the archways in an area void of tooth sockets or where teeth are seated and at the usual location between the labial and lingual sides or surfaces of the appliance. Accordingly, the air holes formed according to the present invention are at all times effective for the purpose intended, i.e., to allow breathing through the mouth when the appliance is in position on the upper and lower teeth. The use of an air hole forming means also provides a unique manner for applying identification to the positioner made of clear material, it being appreciated many different sizes are needed to accommodate the various arch sizes. Indicia such as numbers may be engraved in a surface of the air hole forming means which molds indicia in the positioner during fabrication thereof.

In one form of the method and apparatus according to the invention, a metal insert having a plurality of air hole forming fingers with a hump therealong is incorporated with the mold and used during the molding operation. The insert is placed in the mold at a given location and following the molding operation removed with the appliance after which it may be separated from the appliance. The fingers are arranged substantially along the occlusal plane of the appliance during the molding operation wherein it can be appreciated that the hump is positioned to avoid interference with the models of the teeth in the mold.

A modification of the aforementioned method and apparatus involves the use of an insert where the fingers are straight and where they are arranged in the mold at an angle or approximately parallel to the occlusal plane so that they will form the air holes in clearing relation to the upper and lower teeth.

In another form of the method and apparatus for making the air holes, elastic or flexible members are held in place across the teeth in the mold whereby when the mold parts come together, the members can deform if engaged by teeth so that the air holes likewise when ultimately formed will avoid the tooth sockets or archways formed in the appliance. Again, the flexible members are arranged so that they can be easily separated from the appliance when the appliance is taken from the mold.

It is therefore an object of the present invention to provide a new and improved method and apparatus for making air holes in a tooth positioning and retaining appliance.

A further object of the present invention is in the provision of a method and apparatus for making air holes in a tooth positioning and retaining appliance during the molding of the appliance whereby the air holes will clear the tooth sockets formed in the appliance and be operational during the entire life of the appliance.

A still further object of the present invention is to provide a resilient tooth positioning and retaining appliance having air holes molded therein in such a fashion as to clear the tooth sockets.

Another object of the invention is in the method of uniquely applying identification to a preformed positioner, by molding indicia in an airway which can be easily read where the positioner is made of a clear plastic material.

Other objects, features and advantages of the invention will be apparent from the following detailed disclosure, taken in conjunction with the accompanying sheets of drawings, wherein like reference numerals refer to like parts, in which:

FIG. 1 is an exploded perspective view of a mold according to the present invention and an appliance molded thereby with an insert therein used to mold in air holes during the molding operation;

FIG. 2 is a plan view of the lower half of the mold shown in FIG. 1;

FIG. 3 is a fragmentary enlarged detail sectional view taken through the mold in closed position with the insert removed and to illustrate the configuration of the recess in the lower mold half as it relates to the upper mold half;

FIG. 4 is an enlarged fragmentary sectional view of a closed mold with the molded appliance and the insert in place and taken substantially along line 4—4 of FIG. 1;

FIG. 5 is a plan view of the insert for the mold which molds the air holes in the appliance;

FIG. 6 is a view similar to FIG. 4 but illustrating a modification of the invention wherein the air hole forming means are elastic or flexible members;

FIG. 7 is an exploded side elevational view of another form of mold that may be used to make a custom-made appliance with air holes molded therein;

FIG. 8 is a perspective view of a blank of molding material with the insert placed in the blank and prior to the blank being mounted in a part of the mold;

FIG. 9 is a top plan view of the center section of the mold in FIG. 7 and illustrating the blank and insert in place prior to the molding operation;

FIG. 10 is a top plan view of the appliance following molding after it has been removed from the mold and prior to removal of the air hold forming insert and prior to trimming the appliance to mouth size;

FIG. 11 is an enlarged detail sectional view taken substantially along line 11—11 of FIG. 10 to illustrate the inclination of the air hole forming insert to the occlusal plane; and FIG. 12 is a view similar to FIG. 10 but showing the finished appliance and with the air hole forming insert removed and illustrating the manner in which the air holes are arranged in the appliance.

Referring now to the drawings and particularly to the illustrations of FIGS. 1 to 5, a method and apparatus according to the invention is provided for particularly making a preformed tooth positioning and retaining appliance. The apparatus for making the appliance includes a mold consisting of a lower half 20, an upper half 21, and an insert 22.

An appliance of the type to be made is generally designated by the numeral 23, and it can be a preformed or custom-made appliance. The mold shown in FIGS. 1 to 5 is particularly designed to make preformed appliances of a given size. Any number of mold sizes for respective appliance sizes may be made. The appliances may be molded from any suitable thermoplastic or thermosetting, clear or opaque material that will produce a resilient appliance.

The appliance 23 includes a body 25 having upper and lower archways 26 and 27, each of which is provided with a plurality of tooth sockets 28. It will be appreciated that the tooth sockets in the archways are arranged in ideal arch relationship and preselected positions to urge the teeth received thereby into the preselected positions and ultimately the arches of the wearer into an ideal arch relationship like the preformed positioner in U.S. Pat. No. 3,837,081. The appliance can also be of a type disclosed in U.S. Pat. No. 3,724,075, which has no tooth sockets, and it will be appreciated that any number of arch sizes may be provided in a series of such preformed appliances. Airways or air holes 29 will extend between the labial and lingual sides of the body and generally along the occlusal plane. The air holes may extend essentially parallel to the occlusal plane, as illustrated in FIG. 4, or at an angle to the occlusal plane, as illustrated in FIG. 11. It will be understood the occlusal plane is generally between the arches when the teeth are in occluded or engaged position. As will be more clearly hereinafter described, the airways are molded into the appliance by the insert 22.

The mold would be made of a suitable material such as steel so that it would have a long life and be capable of molding a high number of appliances. The lower half of the mold will mate with the upper half to define a mold cavity for molding the appliance. More specifically, the lower mold half 20 includes a cavity defining a model 31 of the lower arch or teeth, while the upper mold half 21 includes a cavity defining a model 32 of the upper arch or teeth, and when the molds are brought together, the arches would be slightly spaced apart to approximate the relaxed position. Further, the mold halves would include the necessary walls for defining the labial, buccal and lingual boundaries of the appliance as intended to be in finished form for immediate use.

The mold insert 22, which functions to define the air holes or airways in the appliance, is in the shape of a comb and includes a plurality of fingers 35, 36 and 37 extending from a head or support portion 38. The fingers generally extend parallel to each other and are provided therealong with humps 35a, 36a and 37a, respectively, which as can be best seen in FIG. 4, serve to avoid or clear the upper and lower teeth in the anterior portion of the models. While the fingers are illustrated as being rectangular in cross section, it can be appreciated that they may be of any other suitable cross section. As can be seen in FIG. 5, the humps on the fingers are arranged along an arc which is consistent with the upper and lower arch form. It may be appreciated that while three fingers are shown for the insert, any number may be provided. Further, they may be as close together as desired or spaced apart equally or otherwise and other than exactly parallel to each other. By being rectangular in cross section, they provide airways having a greater cross-sectional area without interfering with the arches or tooth sockets. The airways enable a greater breathing capacity than drilled holes.

The mold is provided with suitable recesses for receiving the mold insert 22, and as illustrated in FIGS. 1 to 4, the mold insert is received by a recess 40 formed in the lower mold half 20 and which includes a labial portion 41 at the front side of the archway cavity, and a lingual portion 42 at the rear side of the archway cavity. The labial portion is formed to receive the head of the insert and particularly the support portion 38. In order to assure proper orientation of the insert in view of the humps, a corner of the support portion is flatted at 43 to mate with a flatted portion 44 of the recess. The free ends of the fingers are received in the labial recess portion 42.

The intermediate portions of the fingers are thereby arranged across the dental arches and wherein the humps of the fingers are oriented in an area to provide positive clearance of the teeth and ultimately provide airways through the appliance which do not interfere with the tooth sockets in the archways. In order to facilitate control of the mold insert 22 when handling the mold halves during the molding process, a magnet 46 is mounted in the lower mold half at the insert recess 41 which will provide a holding force to the insert which is of magnetic material when the insert is positioned on the lower mold half. The magnet will thereby function to inhibit displacement of the insert during the closing of the molds. The insert, when in place, will be as illustrated in FIG. 4 so that it can define air holes in the appliance extending between the labial and lingual sides of the appliance generally along the occlusal plane and in what may be termed the freeway spacing of the appliance body which is the material that exists between the upper and lower arches. This freeway spacing is defined as that approximating the relaxed position of the arches which is just short of occlusion. Accordingly, the air holes are molded into the freeway spacing in such a way as to avoid interference with the tooth sockets or the arches. It may be appreciated that while not shown in FIG. 1, the upper mold half 21 is provided with the upper cavity having the teeth positioned in ideal relationships or a smooth arch form to produce a universal positioner as somewhat illustrated in FIG. 4.

The method of making the appliance involves the steps of placing the mold insert 22 on the lower mold half 20, closing the mold by bringing the upper and lower mold halves together as illustrated in FIGS. 3 and 4, and thereafter filling the mold with a suitable moldable material. As seen in FIG. 4, the mold halves, when brought together, lock the mold insert 22 in place. The mold is filled through the entry opening 48 which is defined by a portion of both mold halves when they are together.

While any suitable molding material may be provided, the appliances are preferably made of a thermoplastic material which must be molded while at an elevated temperature. Inasmuch as the material is handled at an elevated temperature during molding, the molds would preferably be preheated, and following the filling of the mold with the material at an elevated temperature in a liquid state, the molds would be cooled to cure the material to a solid state. Thereafter, the mold can be opened wherein the mold halves are separated from one another and the appliance is removed from the mold with the mold insert 22 in place, such as shown in FIG. 1. While the appliance is still at a temperature above room temperature, the insert 22 can be easily removed from the appliance, thereby defining the air holes 29. If a thermosetting material is used, the mold would be filled with the material, after which heat would be applied to cure the material. The word cure as used herein means the application of whatever action is necessary to transform the moldable material to its final usable state.

The mold insert above described would be made of a rigid material that can withstand the temperatures encountered during the molding process. For example, it could be made of metal. In any event, the insert provides a unique manner for applying identification to positioners molded of clear plastic material. Indicia such as numbers can be engraved on a surface of the insert, such as on one or more fingers, and at a point where the numbers could be molded into one or more airways, and which could be read from the outside of the positioner. Thus, identification of the various sizes could be easily made, which is important where small variations exist between some sizes.

Another embodiment is illustrated in FIG. 6 wherein the air hole forming means differs from the insert 22 in that elastic or flexible members 55 are provided. These members may be arranged under some tension and may be anchored to either the lower or upper halves of the mold in a suitable fashion such that they can be easily removed following the molding process. The flexible members 55 are of a type that would maintain substantially the same cross section during the molding process. They cannot be crushable during the filling of the mold, as it is important to maintain the hole size originally intended. The cross section of the members may be of any suitable type such as polygonal or circular, and they must be able to withstand the heat that is involved during the molding process. It can be readily appreciated that in the event a flexible member is engaged by a tooth of the model or the upper or lower arch, it will be displaced and no damage will occur to the tooth or arch, and the molded airway will extend between the teeth or arches. Accordingly, it can be appreciated that the mold insert for defining the air holes can take the form of elastic or flexible members.

While the appliance made by the method and apparatus above described is one that is preformed for use on a patient having arches that generally match the size and form of the appliance, it is also possible to make a custom appliance with air holes or airways according to the invention, and such a method and apparatus will be hereinafter described with attention being given to FIGS. 7 to 12.

The mold illustrated in FIG. 7 includes a lower section 60, an upper section 61, a middle or central section 62 and a mold insert 63. This mold is of a type heretofore known with the exception of the air hole forming insert 63. More specifically, the mold and the method of making a custom-made tooth positioning appliance is disclosed in U.S. Pat. No. 2,775,036. An additional element used in the mold disclosed in the patent is not disclosed herein in that it forms no part of the apparatus and method of the present invention although it will be referred to herein as a spacer which is utilized during the placement of models of lower and upper teeth 64 and 65. More specifically, during the time when the upper and lower models of the dental arches are fixed to the upper and lower mold sections, the spacer is utilized for positioning the models whereby when the models are firmly anchored in place and the upper and lower sections are thereafter manipulated with the center section in the formation of the positioning appliance, the freeway spacing between the teeth is established.

The center section 62 functions to receive a blank 66 of suitable material for making the positioning appliance. This material may be a suitable rubber, plastic or otherwise resilient material which can be formed under pressure and heat during the closing of the molds to ultimately form in the blank the upper and lower archways for receiving the upper and lower teeth. As seen in FIG. 8, the blank 66 may take the form of a length of square-in-cross-section material which can be formed to fit into the cavity or opening 67 of the center section 62, as shown in FIG. 9.

It should be further appreciated that the models of the upper and lower teeth have been produced from a setup which is explained in U.S. Pat. No. 2,775,036, where a model of the teeth of a patient is obtained and the teeth are dissected and reset into their ideal arch relationship which will be the preselected positions that the sockets for the teeth are to take upon use of the appliance. In this respect, the appliance made by the mold of FIG. 7 will be custom fitted for a given patient.

Accordingly, it can be appreciated that the mold in FIG. 7 differs in that it is constructed in three sections and wherein the material for the appliance is in the form of a blank which thereafter is molded by closing of the three sections of the mold and the application of pressure by the platens 70 and 71 until the mold parts come into complete engagement with one another. Guide pins 72 and 73 on the center section 62 respectively mate with openings 74 and 75 to assure the proper orientation of the upper and lower sections relative to the center section and the upper and lower sections relative to each other.

In order to form the air holes or airways in the appliance, the insert 63 is first pressed into the blank of material, as shown in FIG. 8. Preferably, it is pressed into a center portion of the material and in this embodiment at an angle inasmuch as a modified insert is illustrated. The insert 63 includes a plurality of airway fingers 80 which are parallel to one another and which are straight and extend from a head or supporting section 81. In order to guide the placement of the insert in the center mold section 62, a key or tongue 82 is formed on the supporting section 81 for engagement in a keyway 83 formed at the labial side of the blank in the center section 62. A sliding fit is established between the key 82 and the keyway 83 so that during the closing of the mold the insert will seek its own level and if engaged by the teeth of the upper and lower models will move, thereby preventing any damage to the teeth.

At the conclusion of the molding process, the appliance in unfinished form, together with the insert therein, is removed from the mold and takes the form illustrated in FIG. 10 and generally designated by the numeral 85. It can be appreciated that the insert 63 is still in the appliance and, as shown in FIG. 11, is intended to be arranged at an angle to the occlusal plane so that it will miss the teeth when extending between the labial and lingual sides of the body. However, if a greater freeway space existed between the arches, the insert could be generally parallel to the occlusal plane. The insert can then be removed from the unfinished appliance 85, after which the appliance may be trimmed to the form shown in FIG. 12 and generally designated by the numeral 86. As seen in FIG. 12, airways 87 are produced between the labial and lingual surfaces of the appliance body between the upper and lower archways in a similar fashion to the airways as produced in the preformed appliances above described.

It can be further appreciated that the type of air holes defined by the insert 22 can be produced in a custom-made appliance by utilizing an insert of the same configuration. It would also be possible to use a plurality of elastic or flexible members as referred to in connection with the embodiment of FIG. 6 as an insert for the mold of FIG. 7.

The mold of FIG. 7 could also be used to make a custom-made appliance with airways where the material of the appliance is poured into the mold in liquid form. For example, the central section 62 could be placed on the lower section 60, while plastic material in liquid form could be poured into the central section over the lower arch. Thereafter, the upper section 61 could be assembled with the central section where the upper model would penetrate the liquid plastic after which the plastic would be cured. The insert could suitably be mounted in the central section.

It will be understood that modifications and variations may be effected without departing from the scope of the novel concepts of the present invention, but it is understood that this application is to be limited only by the scope of the appended claims.

The invention is hereby claimed as follows:

1. A method for making a tooth positioning and retaining appliance with air holes, said appliance having an arch-shaped body of resilient material with upper and lower archways arranged in ideal arch relationship to receive upper and lower arches of a person, and air holes between the archways and the labial and lingual sides of the body, said method comprising the steps of setting up a mold having upper and lower mold members with models of the upper and lower dental arches to form the archways and an intermediate mold member, supporting air hole forming means by said intermediate mold member to extend at an acute angle to an occlusal plane of at least one of said models, closing the mold, filling the mold with curable molding material, curing the material, opening the mold, removing the molded appliance with the air hole forming means, and removing the air hole forming means from the appliance to define the air holes.

2. A method for making a tooth positioning and retaining appliance with air holes, wherein the appliance includes an arch-shaped body of resilient material having upper and lower archways arranged in ideal arch relationship to receive upper and lower arches of a person, and air holes between the archways and the labial and the lingual sides of the body, said method comprising the steps of setting up a mold having upper and lower mold members with models of the upper and lower dental arches to form the archways with said mold members having narrow recesses therebetween for opposite ends of an insert member which is generally flat but having a humped portion intermediate said ends, disposing said ends of the insert member in said recesses with said humped portion being disposed across a cavity of said mold and located adjacent an anterior portion of one of said arches to the insert member clears said arches, closing the mold, filling the mold with curable molding material, curing the material, opening the mold, removing the molded appliance with the insert member, and removing the insert member from the appliance to define the air holes.

3. The method of claim 2 wherein said insert member has the form of plural fingers interconnected at one end and each of said fingers has a hump.

4. A method for making a tooth positioning and retaining appliance with air holes, wherein the appliance includes an arch-shaped body of resilient material having upper and lower archways arranged in ideal arch relationship to receive upper and lower arches of a person, and air holes between the archways and the labial and lingual sides of the body, said method comprising the steps of setting up a mold having upper and lower mold members with models of the upper and lower dental arches to form the archways, placing flexible air hole forming means in the mold between interior portions of said arches to form the air holes, closing the mold, pressing said models against said forming means, deforming said means between said arches, filling the mold with curable molding material, curing the material, opening the mold, removing the molded appliance with the air hole forming means, and removing the air hole forming means from the appliance to define the air holes.

5. A method for making a tooth positioning and retaining appliance with air holes, wherein the appliance includes an arch-shaped body of resilient material having upper and lower archways arranged in ideal arch relationship to receive upper and lower arches of a person, and air holes between the archways and the labial and lingual sides of the body, said method comprising the steps of setting up a mold having upper and lower mold members with models of the upper and lower dental arches to form the archways with said mold members having narrow recesses therebetween for opposite ends of an insert member which is generally flat and extends at an acute angle to the occlusal plane of at least one of said models, disposing said ends of the insert member in said recesses with said humped portion being disposed across a cavity of said mold and located adjacent an anterior portion of one of said arches so the insert member clears said arches, closing the mold, filling the mold with curable molding material, curing the material, opening the mold, removing the molded appliance with the insert member, and removing the insert member from the appliance to define the air holes.

6. A method of making a custom tooth positioning and retaining appliance with air holes from a blank of moldable material in a three-part mold having an air hole insert wherein the appliance to be made includes an arch-shaped body of resilient material having upper and lower achways to receive upper and lower arches of a person, and air holes between the archways and the labial and lingual sides of the body, said method comprising the steps of mounting models of the arches in the mold such that when the mold is closed a freeway spacing will be defined between the arches, forcing the air hole insert into the blank of material, placing the blank of material with the insert therein in the mold such that the location of the insert is guided by the mold, closing the mold to effect the forming of the arches in the blank in relation to the air holes, opening the mold, removing the appliance, and separating the insert from the appliance.

* * * * *